United States Patent
Vahle

(10) Patent No.: US 11,627,929 B2
(45) Date of Patent: Apr. 18, 2023

(54) SYSTEM AND METHOD FOR RECORDING A POSITRON EMISSION TOMOGRAPHY IMAGE DATA SET

(71) Applicant: Siemens Healthcare GmbH, Erlangen (DE)

(72) Inventor: Thomas Vahle, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 332 days.

(21) Appl. No.: 17/082,746

(22) Filed: Oct. 28, 2020

(65) Prior Publication Data

US 2021/0121148 A1    Apr. 29, 2021

(30) Foreign Application Priority Data

Oct. 29, 2019   (DE) .......................... 102019216648.2

(51) Int. Cl.
| | | |
|---|---|---|
| *A61B 6/04* | (2006.01) | |
| *A61B 5/055* | (2006.01) | |
| *A61B 6/00* | (2006.01) | |
| *G01R 33/48* | (2006.01) | |
| *A61B 6/03* | (2006.01) | |

(Continued)

(52) U.S. Cl.
CPC ............ *A61B 6/5235* (2013.01); *A61B 5/055* (2013.01); *A61B 6/037* (2013.01); *A61B 6/5247* (2013.01); *A61B 6/5264* (2013.01); *A61B 6/5288* (2013.01); *G01R 33/481* (2013.01); *G01R 33/4828* (2013.01); *G01R 33/5607* (2013.01); *G01R 33/5613* (2013.01); *G06T 11/005* (2013.01)

(58) Field of Classification Search
None
See application file for complete search history.

(56) References Cited

U.S. PATENT DOCUMENTS 9,168,015 B2 * 10/2015 Stearns ................ A61B 6/5282
9,400,317 B2 *  7/2016 Glielmi .................. G06T 5/008

(Continued)

OTHER PUBLICATIONS

Catana, "Motion Correction Options in PET/MRI" Seminars in Nuclear Medicine, vol. 45, Issue 3, May 2015, pp. 212-223 (Year: 2015).*

(Continued)

*Primary Examiner* — Colin T. Sakamoto
(74) *Attorney, Agent, or Firm* — Banner & Witcoff Ltd.

(57) ABSTRACT

In a method for recording a PET image data set, an overall recording area is moved continuously through the FOV at a constant movement speed, an attenuation map of the overall recording area being used to reconstruct the PET image data record from the PET raw data. The magnetic resonance data of a slice of the patient currently located within the FOV and movement status information relating to a cyclical movement of the patient are recorded simultaneously with recording the PET raw data. A movement status class is assigned to the PET raw data and the magnetic resonance data in each case. Using the magnetic resonance data assigned to the different movement status classes, attenuation maps of the patient are determined for the different movement status classes and applied to the PET raw data assigned to the corresponding movement status class to reconstruct the PET image data set.

12 Claims, 3 Drawing Sheets

(51) Int. Cl.
  *G01R 33/56*  (2006.01)
  *G01R 33/561* (2006.01)
  *G06T 11/00*  (2006.01)

(56) References Cited

U.S. PATENT DOCUMENTS

| | | | | |
|---|---|---|---|---|
| 9,427,206 | B2* | 8/2016 | Stearns | A61B 5/085 |
| 9,990,741 | B2* | 6/2018 | Panin | A61B 6/5247 |
| 10,504,250 | B2* | 12/2019 | Wang | G06T 11/005 |
| 10,690,782 | B2* | 6/2020 | Wang | A61B 6/5205 |
| 10,839,567 | B2* | 11/2020 | Wang | A61B 6/5264 |
| 2014/0056500 | A1* | 2/2014 | Bal | G06T 11/005 |
| | | | | 382/131 |
| 2014/0153806 | A1* | 6/2014 | Glielmi | G01R 33/481 |
| | | | | 382/131 |
| 2014/0243653 | A1* | 8/2014 | Fenchel | A61B 5/055 |
| | | | | 600/411 |
| 2015/0178906 | A1* | 6/2015 | Stearns | G06T 7/32 |
| | | | | 382/131 |
| 2015/0196266 | A1* | 7/2015 | Fenchel | A61B 6/5247 |
| | | | | 600/411 |
| 2015/0289832 | A1* | 10/2015 | Bal | A61B 6/5264 |
| | | | | 600/407 |
| 2016/0029990 | A1* | 2/2016 | Stearns | A61B 5/0522 |
| | | | | 600/411 |
| 2016/0069973 | A1* | 3/2016 | Fenchel | G01R 33/481 |
| | | | | 324/309 |
| 2017/0091963 | A1* | 3/2017 | Panin | A61B 6/5264 |
| 2019/0101655 | A1* | 4/2019 | Wang | A61B 6/037 |
| 2019/0236816 | A1* | 8/2019 | Wang | A61B 6/037 |
| 2020/0098152 | A1* | 3/2020 | Wang | A61B 6/5288 |

OTHER PUBLICATIONS

Lu et al., "Whole-body continuous-bed-motion PET list-mode reconstruction with non-rigid event-by-event respiratory motion correction" Journal of Nuclear Medicine May 2019, 60 (supplement 1) 105 (Year: 2019).*

Rahmim, Arman et al. "Dynamic whole-body PET imaging: principles, potentials and applications" European Journal of Nuclear Medicine and Molecular Imaging, vol. 46, pp. 501-508, 2019 // ISSN 1619-7070.

Catana, Ciprian "Motion Correction Options in PET/MRI" Seminars in Nuclear Medicine, vol. 45, No. 3, pp. 212-223, 2015 // https://doi.org/10.1053/j.semnuclmed.2015.01.001.

Speier, P. et al. "PT-Nav: A Novel Respiratory Navigation Method for Continuous Acquisition Based on Modulation of a Pilot Tone in the MR-Receiver" ESMRMB 129:97-98, 2015. doi: 10.1007/s10334-015-0487-2.

Rigie, David et al. "Cardiorespiratory Motion-Tracking via Self-Refocused Rosette Navigators" Magnetic Resonance in Medicine, vol. 81, No. 5, pp. 2947-2958, 2019 // ISSN 0740-3194.

German action dated Jun. 19, 2020, Application No. 10 2019 216 648.2.

* cited by examiner ies have however also been proposed in the meantime, with which a simultaneous recording of PET raw data and magnetic resonance data (MR data) is possible, which can also be referred to as combined magnetic resonance PET devices. Here a gradient coil arrangement of the magnetic resonance portion of the magnetic resonance PET device can be cut through centrally, for instance, in order to create space for a PET detector ring, wherein approaches for embodiments which are at least sufficiently transparent for the PET photons and the photon detectors influencing the magnetic resonance fields as little as possible have also been carried out for the PET imaging. A PET detector ring is frequently inserted into the patient receptacle of a main magnet unit.

SYSTEM AND METHOD FOR RECORDING A POSITRON EMISSION TOMOGRAPHY IMAGE DATA SET

CROSS REFERENCE TO RELATED APPLICATIONS

This patent application claims priority to German Patent Application No. 102019216648.2, filed Oct. 29, 2019, which is incorporated herein by reference in its entirety.

BACKGROUND

Field

The disclosure relates to a method for recording a positron emission tomography (PET) image data set of an overall recording area of a patient with a magnetic resonance PET device configured to simultaneously record PET raw data and magnetic resonance data. In addition, the disclosure relates to a magnetic resonance PET device, a computer program and an electronically readable data carrier.

Related Art

Image recording devices, which combine the positron emission tomography (PET) with other imaging modalities, have already been proposed in the prior art. Here combined PET-CT devices, in other words combinations with computed tomography, are firstly known since the computed tomography is particularly suited to determining the attenuation maps ($\mu$-maps) of the patient used to correct recorded PET raw data with respect to the scattering in the body. This is due to the fact that the x-ray scattering and the scattering of the PET photons are closely related. Image recording devices have however also been proposed in the meantime, with which a simultaneous recording of PET raw data and magnetic resonance data (MR data) is possible, which can also be referred to as combined magnetic resonance PET devices. Here a gradient coil arrangement of the magnetic resonance portion of the magnetic resonance PET device can be cut through centrally, for instance, in order to create space for a PET detector ring, wherein approaches for embodiments which are at least sufficiently transparent for the PET photons and the photon detectors influencing the magnetic resonance fields as little as possible have also been carried out for the PET imaging. A PET detector ring is frequently inserted into the patient receptacle of a main magnet unit.

For magnetic resonance PET devices of this type, methods have also already been proposed to determine the attenuation maps ($\mu$-maps) required to correct the PET raw data from magnetic resonance data. Here a material decomposition in particular can be carried out in magnetic resonance data of the anatomy of the patient, wherein specific attenuation values for the attenuation maps are assigned to each material. Fat and water images of the patient or of the relevant recording area are frequently produced here, wherein embodiments in which a separate consideration of bones and/or further materials also takes place are also conceivable.

PET recording procedures are also particularly popular in diagnostic processes on patients, in which larger areas of a patient, in particular the entire body of the patient, is recorded in order to produce a corresponding PET image data set. Here various approaches are known in the prior art for such recording procedures, in which the overall recording area of the patient exceeds the field of view of the corresponding PET image recording device. Therefore what is known as the step-and-shoot method is used, in which the patient couch is moved step by step and successively different, for instance 25 cm long partial recording areas of the patient are measured. For rapid whole-body PET protocols it has also been proposed in the meantime to provide a continual movement of the patient couch. In order to be able to record a sufficient number of PET raw data, extremely low speeds of the patient couch of for instance approx. 1 mm/s are used. On account of the resulting long recording time, for instance 6 to 10 minutes, it is not possible for the patient to hold his breath for this time and the PET raw data is therefore subjected to the breathing movement.

With computed tomography PET devices, the computed tomography-based attenuation map is determined here before recording the actual PET raw data either while breath is being held or while breathing freely. The recording of the corresponding CT data only requires a few seconds here. This produces a single attenuation map which either only adjusts to a movement phase of the breathing movement or contains motion blurs.

In this regard whole-body PET protocols which use continuous patient couch movements use the same strategy as for the combination of PET and CT; this means that an individual attenuation map is to be recorded in a rapid measurement either when breath is being held or while breathing freely. The resulting difference between the movement-influenced PET raw data and the attenuation maps to be used can result in artifacts in the resulting PET image data sets. This can result in problems in the diagnostics, for instance with respect to small lesions. Here, as one approach it has so far only been proposed to carry out a movement correction based on the PET raw data, but the PET raw data indicating a less anatomical structure is typically poorly suited to a reliable determination of movement information.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
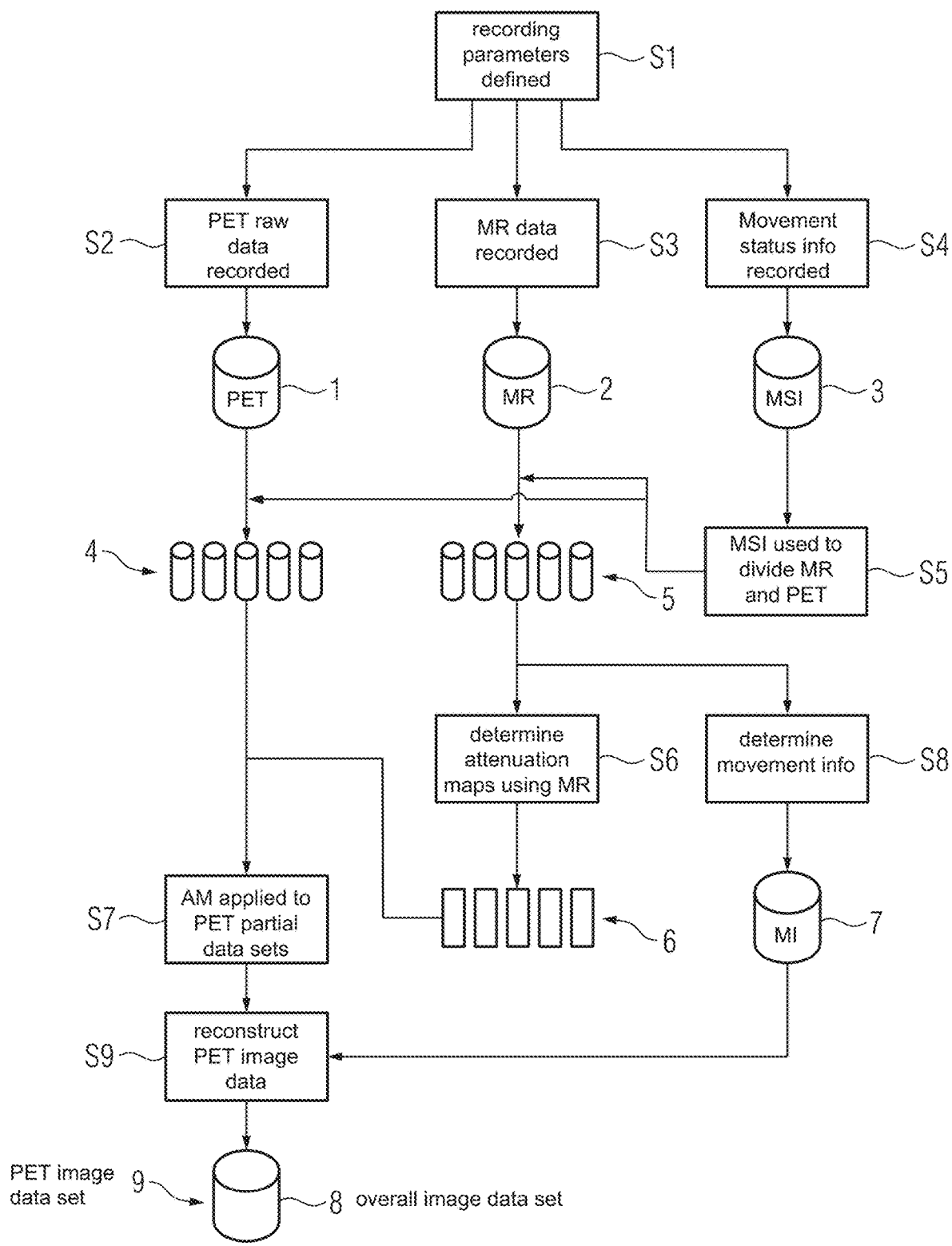
FIG. 1 is a flowchart of a method according to an exemplary embodiment.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the disclosure is to enable higher quality PET image data sets to be determined in large recording areas. In aspects of the disclosure, a method, a magnetic resonance PET device, a computer program and an electronically readable data carrier are provided to determine higher quality PET image data sets.

An aspect of the present disclosure relates to a method for recording a positron emission tomography (PET) image data set of an overall recording area of a patient with a magnetic resonance PET device configured to simultaneously record PET raw data and magnetic resonance data. The overall recording area of the patient may exceed the size of the field of view of the magnetic resonance PET device and the overall recording area for recording PET raw data may be moved continuously through the field of view at a constant movement speed. At least one attenuation map of the overall recording area may be used to reconstruct the PET image data set from the PET raw data.

In an exemplary embodiment, a method for recording a positron emission tomography (PET) image data set includes:

magnetic resonance data of a slice of the patient currently located within the field of view and at least one movement status information relating to a cyclical movement of the patient are recorded simultaneously with recording the PET raw data, wherein a movement status class described by the movement status information determined during its recording is assigned to the PET raw data and the PET magnetic resonance data in each case, and by using the magnetic resonance data assigned to different movement status classes, attenuation maps of the patient are determined for the different movement status classes and are applied to the PET raw data assigned to the corresponding movement status class in order to reconstruct the PET image data set in each case.

Here the movement status information relates particularly advantageously to at least the breathing movement of the patient but can in many instances also relate to the heart movement of the patient as a cyclical or periodic movement. Cyclical movements of this type are characterized in that they can be described by a cyclically repeating sequence of movement phases, which essentially repeat the same with the patient. Specific movement statuses of the patient are present within these different movement phases so that movement status classes which summarize similar movement statuses of the patient, which thus lie within a specific tolerance deviation, can be defined. In particular, two to ten movement status classes, for instance five movement status classes, can be defined for the breathing.

In one or more aspects of the disclosure, with the continual movement of the patient couch, only a very slow speed of the patient couch is present, for instance in the range of 0.5 to 1.5 mm/s, so that PET raw data and magnetic resonance data are recorded from specific areas over a specific period of time, in particular covering at least one complete movement cycle of the cyclical movement, for instance one breathing cycle. In an aspect of the disclosure, the cyclical movement of the patient is monitored during the recording procedure, so that it is possible to subdivide the PET raw data similarly to the magnetic resonance data into various movement status classes, in particular breathing movement status classes, possibly also heart beat movement status classes, on the basis of the movement status information describing the current movement status of the patient. This in turn allows an attenuation map to be determined for each movement status class from the magnetic resonance data, which can then be applied to the PET raw data assigned to the same movement status class within the scope of the reconstruction in order to obtain high quality PET image data sets.

In an aspect of the disclosure, during the entire recording procedure, thus the entire continuous movement of the patient couch, a monitoring of the at least one cyclical movement of the patient takes place, in order on this basis to determine movement-resolved attenuation maps, in particular one attenuation map per movement status class. On this basis PET image data sets of the overall recording area which include the movement can be reconstructed with a higher quality.

In an exemplary aspect, the overall recording area corresponds particularly advantageously to the entire body of the patient, so that a rapid whole-body screening is achieved with a continual movement of the patient couch including movement correction.

In an exemplary aspect, it is essentially possible to provide special sensors as the source of the movement status information, for instance what are known as breathing belts or other breathing sensors, in particular in the patient couch. However, these supply rather inaccurate movement status information. It is essentially also conceivable to carry out navigator sequences with the magnetic resonance portion of the combined magnetic resonance PET device, which however requires complex adjustments to the magnetic resonance sequences also with respect to the recording of the magnetic resonance data.

In an exemplary embodiment, the movement status information is recorded from navigator data of a pilot tone navigator. In order to measure a pilot tone navigator, in an exemplary embodiment, a coherent pilot tone signal is emitted by means of an independent signal source, for instance a pick-up coil, wherein a CW high frequency signal (CW—Continuous Wave) can be used as a pilot tone signal, the pilot tone frequency of which lies outside of the frequency band of the magnetic resonance signal and the field of view, but within the frequency band received by the receive coil elements. Here the pilot tone signal has an amplitude which can be detected in the linear operating range of the receiver of the magnetic resonance portion of the magnetic resonance PET device. In one or more embodiments, the pilot tone signal received by the receive coil elements can be adjusted to a model, by which at least one model parameter can be used as a pilot tone navigator. Described fundamentally are pilot tone navigators for instance in the conference paper "PT-Nav: A novel respiratory navigation method for continuous acquisitions based on modulation of a pilot tone in the MR-receiver" by P. Speier et al., Proc. ESMRMB 129: 97-98, 2015. The use of a pilot tone navigator has the advantage that highly accurate movement status information can be determined, without the measurement of the magnetic resonance data having to be modified, for instance.

In an exemplary embodiment, a provision can be made for consecutively recorded slices to overlap, in particular slices recorded consecutively in terms of time to overlap at least by 80%, preferably at least by 90%. This means that the slice thickness, which can lie in particular in the range of 3 to 10 mm, can preferably amount to 5 mm, and/or the movement speed of the patient couch, which can lie in particular in the range of 0.5 to 1.5 mm/s, are selected so that with slices of the magnetic resonance data recorded consecutively in terms of time, an overlap of at least 80%, preferably at least 90%, is present. In other words the slice distance for slices of the magnetic resonance data recorded consecutively in terms of time is set to a negative value, for instance −90%, so that on the one hand the PET raw data and also the magnetic resonance data are recorded sufficiently slowly, on the other hand however an oversampling of the overall recording area takes place by means of the magnetic resonance data so that magnetic resonance data of the same recorded partial recording area of the overall recording area can be sorted into different movement status classes and the magnetic resonance data of all movement status classes thus covers the overall recording area.

In this way attenuation maps of the complete overall recording area can be generated for each movement status class and can be applied to corresponding PET raw data similarly of the overall recording area which is assigned to the same movement status class. Simple calculations are thus allowed on the overall recording area.

To record the magnetic resonance data, a Dixon technique can be used particularly advantageously, wherein in order to determine attenuation data from the magnetic resonance data, at least fat and water images are determined for the movement status classes. Dixon techniques are based on the small difference in the Lamor frequency between fat and water or other materials (chemical displacement) and allow magnetic resonance images to be reconstructed which only contain the fat portions or only the water portions in the slice so that a material decomposition takes place effectively. This material decomposition can be used advantageously within the scope of the present disclosure in order to generate attenuation maps, in which corresponding attenuation values are assigned to the different materials or the relative composition per voxel. Here further materials or material classes, for instance bones, can also be taken into account.

In order to enable a rapid recording of the magnetic resonance data, one or more embodiments of the present disclosure can use a FLASH (Fast low angle shot) magnetic resonance sequence. In particular, it is therefore possible to use a FLASH Dixon technique to record the magnetic resonance data during the recording of the PET raw data.

In an exemplary embodiment, individual partial image data sets of the PET image data set assigned to the different movement status classes are combined to form a movement-corrected overall image data set on account of the movement status information and/or the magnetic resonance data. This means that all PET raw data is then included in a shared overall image data set, which can in particular on its own form the PET image data set in order to allow the highest possible image data quality of the PET image data set. Provision can be made here specifically that, for the movement status classes, by registering the magnetic resonance data assigned to different movement status classes, movement information describing the relative movement is determined and used for movement correction. This means that movement information, for instance movement vector fields, are generated on the basis of the significantly more accurate and structured magnetic resonance data reproducing the anatomy, so that an excellent movement correction is enabled and overall a movement-corrected whole-body reconstruction of the PET raw data can take place. It should be noted that it can also be expedient in application cases to maintain the movement-resolved existing partial image data sets likewise further as part of the PET image data set, if expedient diagnostic information can be derived herefrom. In this case, a movement-resolved reconstruction is then achieved.

In an exemplary embodiment, a retrospective gating explicitly or implicitly is performed to determine less influenced PET image data sets from movements. For instance, sufficiently broadly defined movement status classes can be used, for instance a movement status class comprising movement statuses which lie as close as possible to the end expiration, and/or a movement status class which is defined so that it contains at least one predetermined portion of the PET raw data, for instance 40%, preferably similarly about the end expiration during the breathing movement. It is also possible, however, to reconstruct the PET image data set from PET raw data assigned to the movement status classes, for which the movement statuses according to a corresponding criterion are sufficiently similar.

Aspects of the disclosure also relates to a magnetic resonance PET device, having a controller which is configured to execute the inventive method. Here the controller can comprise at least one processor and at least one storage means.

In an exemplary embodiment, the controller includes a sequencer for playing out magnetic resonance sequences and a magnetic resonance receiver for recording the magnetic resonance data similarly to a PET receiver for recording the PET raw data. These essentially known components control corresponding further components of the magnetic PET device or take information herefrom. The movement status information is determined by way of a movement status determination unit (movement status determinator). The movement status determination unit can form a part of the magnetic resonance receiver as a pilot tone unit. The controller of the inventive magnetic resonance device can further have an assignment unit (assigner) for assigning a movement status class to magnetic resonance data and PET raw data, so that in the assignment unit the PET raw data and the magnetic resonance data are finally sorted according to movement status classes. Furthermore, an attenuation map determination unit (attenuation map determinator) can be provided to determine the attenuation maps for the movement status classes from the magnetic resonance data and a movement information determination unit (movement information determinator) if movement information is to be determined. In a reconstruction unit (reconstructor), the attenuation maps are used to reconstruct PET image data sets, wherein a fusion unit can also be provided in addition to or integrated in the reconstruction unit, where on the basis of the movement information the PET image data of the various movement status classes can be merged. Further functional units are naturally also conceivable for other conceivable steps of the inventive method, for instance also a setting unit, in which the recording parameters, in particular the movement speed of the patient couch and/or the slice thickness, can be selected so that a desired overlap is produced between slices recorded adjacent to one another in terms of time.

An inventive computer program can be loaded directly into a storage device of a controller of a magnetic resonance PET device, for instance, and has programming means in order to execute the steps of an inventive method if the computer program is executed in the controller of the magnetic resonance PET device.

The computer program can be stored on an inventive electronically readable data carrier which therefore comprises electronically readable control information stored thereon, which comprises at least one inventive computer program and is configured such that with the use of the data carrier in a controller of a magnetic resonance PET device, said control information carries out an inventive method. The data carrier is preferably a non-transient data carrier, for example, a CD-ROM.

With reference to FIG. 1, a whole-body PET scan of a patient is to be recorded, thus a PET image data set of the whole-body of the patient is to be produced by means of a magnetic resonance PET device, therefore an examination device, with which magnetic resonance data and PET data can be recorded simultaneously from a field of view which essentially corresponds advantageously to PET and magnetic resonance. A method according to an exemplary embodiment is described below with reference to FIG. 1.

In a step S1, recording parameters are defined for this and the recording is then started. The recording parameters currently also comprise a movement speed of the patient couch, since the PET raw data (and simultaneously thereto magnetic resonance data) is recorded during a continuous, slow couch movement so that the entire body of the patient has moved through the field of view.

After starting the movement of the patient couch, PET raw data 1 is recorded continuously according to step S2. However, in a step S3 a simultaneous recording of magnetic resonance data also takes place in parallel hereto, wherein in each case a slice of a few millimeters thick, for instance 5 mm thick, is recorded, wherein the movement speed of the patient couch is selected so that an overlap of at least 90% always exists with slices which are recorded consecutively in terms of time. The magnetic resonance data 2 is recorded with a FLASH magnetic resonance sequence and a Dixon technique, so that in particular water and fat images can be reconstructed therefrom.

Finally, in a step S4 up-to-date movement status information 3 with respect to the current breathing movement status of the patient is always recorded in parallel with recording the PET raw data 1 and the magnetic resonance data 2. To this end, a pilot tone navigator is currently used, by a transmit means, for instance a pick-up coil, emitting a pilot tone signal, which lies outside of the frequency range relevant to the magnetic resonance signals, but within the frequency range which can be received by the receive coils of the magnetic resonance PET device, said pilot tone signal being received by the receive coil elements of the magnetic resonance PET device and possibly being evaluated by a pilot tone unit, as a movement status determination unit, integrated into the magnetic resonance receive unit, in order to determine the movement status information 3.

Already during the data recording or after its conclusion, the movement status information 3 can be used in a step S5 to divide the PET raw data 1 and the magnetic resonance data 2 into partial data sets 4, 5, the PET raw data 1 or magnetic resonance data 2 of which are then assigned in each case to one of here five movement status classes, for instance. Since the breathing movement represents a cyclical movement, similar movement statuses which occur repeatedly can divide into movement status classes, here by way of example five movement status classes. The movement status information 3 allows recorded PET raw data 1 and magnetic resonance data 2 according to its movement status to be sorted into corresponding movement status classes so that the partial data sets 4, 5 are produced.

The partial data sets 5 of the magnetic resonance data 2 are now currently used initially in a step S6, in order to determine attenuation maps 6 of the overall recording area, here in other words of the entire body of the patient, for each movement status class. This takes advantage of the fact that in step S3 a Dixon technique has been used, so that on account of the water and fat contents in the respective voxel for instance individual voxels are assigned attenuation values (µ-values) which describe the scatter and attenuation behavior of the PET photons in the body of the patient. It should still be noted at this point that magnetic resonance data 2 exists for all movement status classes and body positions on account of the described slow movement speed and the resulting high overlap between adjacent slices.

The attenuation maps 6 are used in step S7 in the reconstruction of PET image data from the PET raw data 1 for correcting the PET raw data 1, specifically applied in each case to the partial data set of the same movement status class.

The magnetic resonance data 2 or the partial data sets 5 are also used further however in step S8 in order to determine movement information 7, in particular movement vector fields, which describe the movement between two movement status classes. To this end, the magnetic resonance images of individual partial data sets 5 are registered with one another, from which the movement vector fields result directly. This movement information 7 can then be used in a step S9 to merge the partial data sets 4 of the PET raw data 1 in a movement compensated manner to form an overall image data set 8 as a PET image data set 9. Consequently, the magnetic resonance data 2 recorded in parallel is used by using the movement status information 3 to determine attenuation maps 6 for all movement status classes and also to allow a movement-corrected merging of all PET raw data 1.

Figure 2:
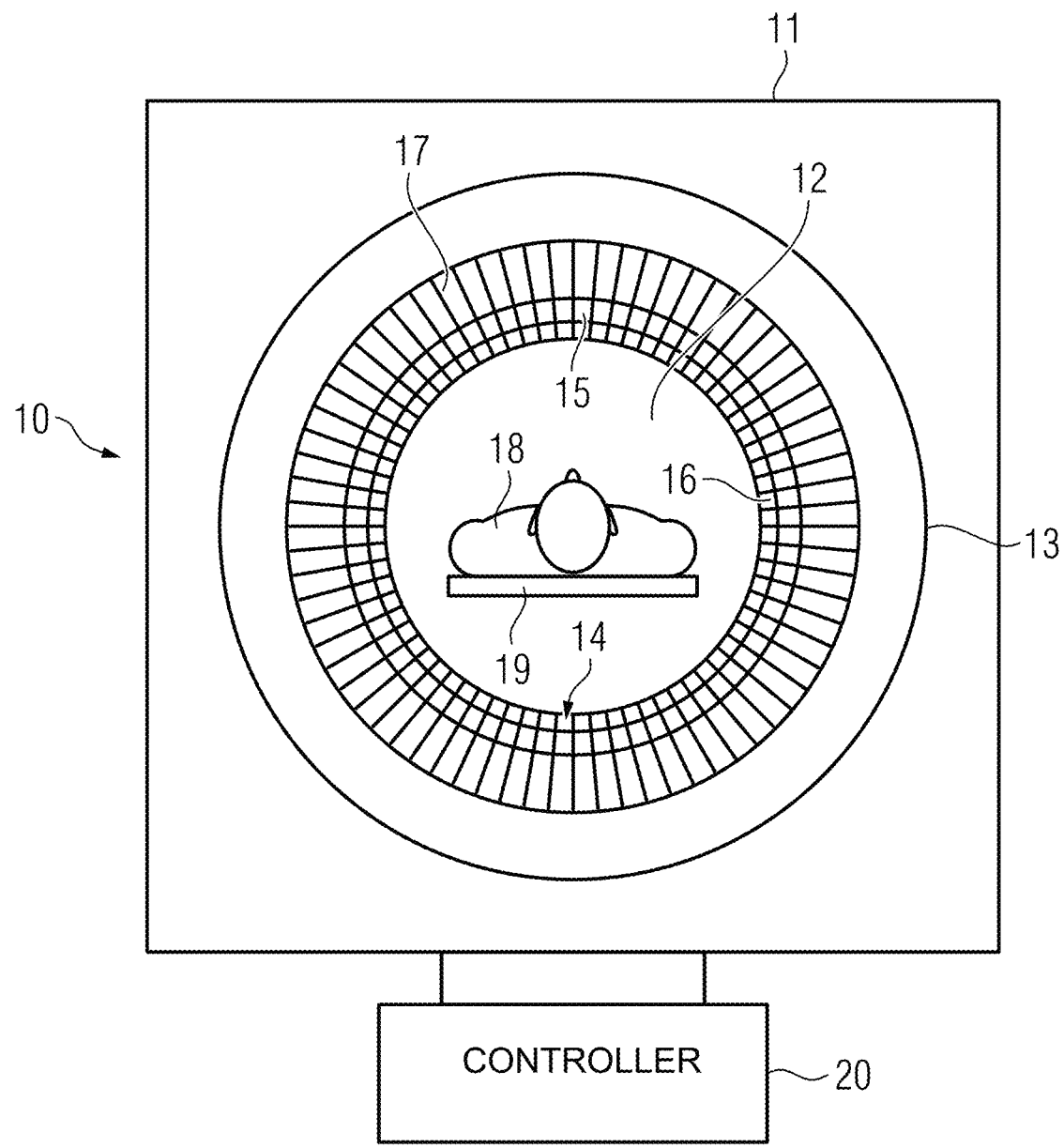
FIG. 2 illustrates a magnetic resonance PET device according to an exemplary embodiment.

FIG. 2 shows a schematic diagram of a magnetic resonance PET device 10, in a schematic cross-section, according to an exemplary embodiment. Such a combined magnetic resonance PET device 10 has the advantage of both magnetic resonance data 2 and also PET raw data 1 being able to be obtained isocentrically. In other words, the magnetic resonance data 2 and the PET raw data 1 are inherently registered with one another.

In an exemplary embodiment shown in FIG. 2, the magnetic resonance PET device 10 includes a main magnet unit 11, in which the superconducting basic field magnet is arranged. The main magnet unit 11 defines the patient receptacle 12 essentially centrally, wherein a coil arrangement 13 is typically also provided within the cylindrical basic field magnet, said coil arrangement comprising a gradient coil arrangement and a radio frequency coil arrangement. A number of PET detection units 14 arranged opposite one another in pairs about the longitudinal direction are currently also arranged within the main magnet unit 11, however. The PET detection units 14 can consist for instance of an APD photo diode array 15 with an upstream array comprising LSO crystals 16 and an electric amplifier circuit 17. Other detection units 14, which use photodiodes, crystals and devices of a different type are however also conceivable. The main magnet unit 11 can be referred to as, or a component of, a magnetic resonance PET scanner.

The patient 18 can be moved into the patient receptacle 12 by means of a patient couch 19, this means that the patient couch 19 can be moved in the longitudinal direction through the patient receptacle 12. Along the longitudinal direction of the patient receptacle 12, a first field of view, namely the homogeneity volume of the magnetic resonance portion, and a second field of view, namely that of the PET detection units 14, are defined, wherein the first field of view and the second field of view currently correspond at least essentially. This can be achieved by a corresponding adjustment of the arrangement density of the PET detection units 14 along the longitudinal direction.

The operation of the magnetic resonance PET device 10 is controlled by a controller 20 which is also configured to carry out the inventive method (of FIG. 1).

Figure 3:
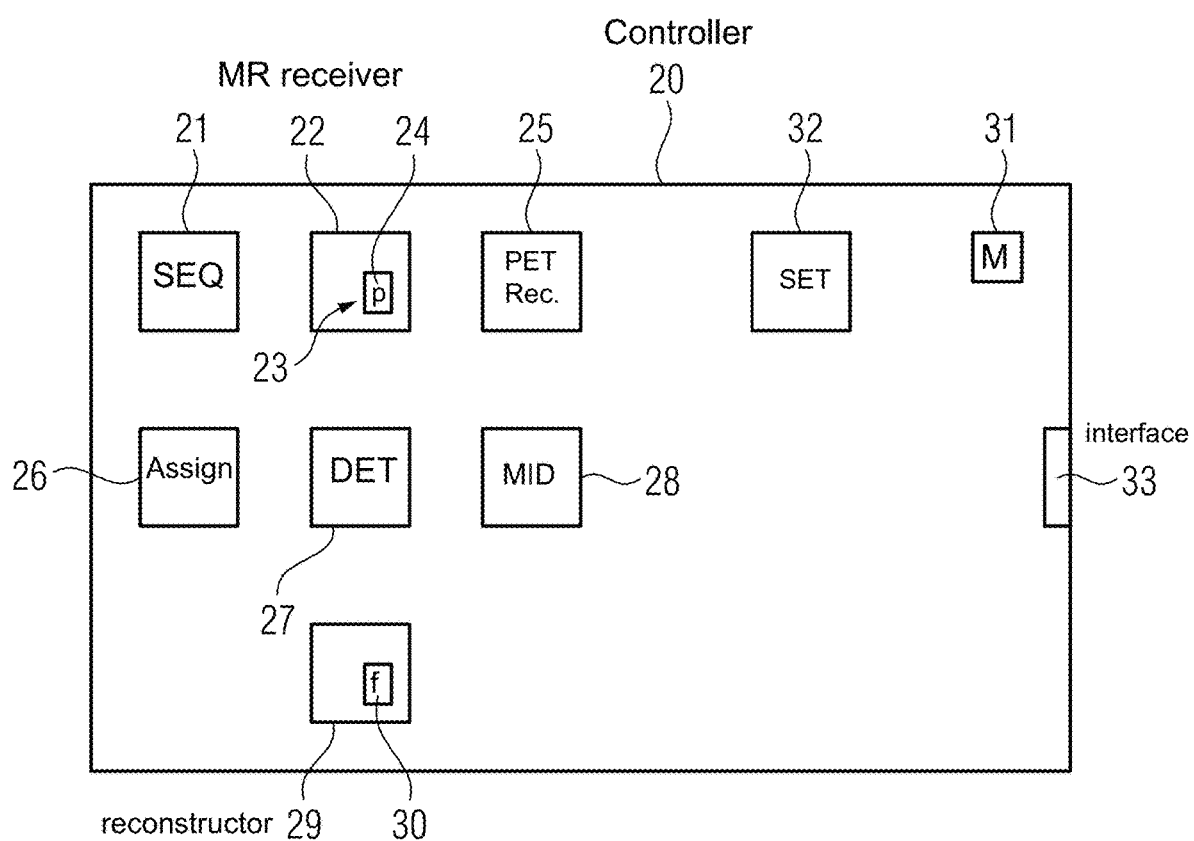
FIG. 3 illustrates a controller, according to an exemplary embodiment, of the magnetic resonance PET device of FIG. 2.

FIG. 3 shows an exemplary embodiment of the controller 20. In an exemplary embodiment, the controller 20 includes, for data acquisition, a sequencer 21 and a magnetic resonance receiver 22, which are configured to carry out the step S3 of the method of FIG. 1. The movement status determination unit 23, here a pilot tone unit 24, is currently integrated into the magnetic resonance receiver 22. In an exemplary embodiment, the controller 20 includes processor circuitry that is configured to perform one or more functions and/or operations of the controller 20.

The PET raw data 1 is recorded in step S2 by a corresponding PET receiver 25.

In an exemplary embodiment, the controller 20 also includes an assignment unit 26 configured to assign PET raw data 1 and magnetic resonance data 2 to movement status classes based on the movement status information 3 (Step S5). The developing partial data sets 5 are now firstly used according to step S6 in an attenuation map determination unit 27 and according to step S8 in a movement information determination unit 28. The attenuation maps 6 and movement information 7 determined therein are in turn used in a reconstruction unit 29, in order to determine the PET image data set 9, wherein a corresponding fusion unit 30 is currently integrated into the reconstruction unit 29.

In order to store the corresponding data while converting the inventive method, at least one storage means (e.g. memory) 31 is also provided, wherein the various functional units 21 to 30 are implemented by at least one processor of the controller 20.

In an exemplary embodiment, the controller 20 also includes one or more further control units and functional units, such as a setting unit 32 configured to carry out the step S1. Reconstructed image data sets, in particular also the PET image data set 9, can be output by way of an interface 33, for instance to an image archiving system and/or a display means and/or a diagnostic workstation.

Although the disclosure has been illustrated and described in greater detail with the preferred exemplary embodiment, the disclosure is not restricted by the examples disclosed and other variations can be derived therefrom by the person skilled in the art without departing from the protective scope of the disclosure.

Any connection or coupling between functional blocks, devices, components of physical or functional units shown in the drawings and described hereinafter may be implemented by an indirect connection or coupling. A coupling between components may be established over a wired or wireless connection. Functional blocks may be implemented in hardware, software, firmware, or a combination thereof.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM).

The memory can be non-removable, removable, or a combination of both.

The invention claimed is:

1. A method for recording a positron emission tomography (PET) image data set of an overall recording area of a patient, the method comprising:
using a magnetic resonance PET device, simultaneously recording PET raw data, magnetic resonance data of corresponding slices of the patient currently located within a field of view of the magnetic resonance PET device, and movement status information relating to one of a plurality of cyclical movements of the patient, the overall recording area of the patient exceeding a size of the field of view of the magnetic resonance PET device, wherein the overall recording area for recording the PET raw data is moved continuously at a constant movement speed through the field of view;
assigning a movement status class, based on the movement status information, to the PET raw data and the magnetic resonance data associated with each of the plurality of cyclical movements;
based on the magnetic resonance data assigned to the different movement status classes:
determining attenuation maps of the patient for each of the different movement status classes, and
applying the attenuation maps to the PET raw data assigned to the corresponding one of the different movement status classes; and
reconstructing the PET image data set from the PET raw data based on at least one of the attenuation maps of the overall recording area.

2. The method as claimed in claim 1, wherein the movement status information relating to a breathing movement of the patient and/or a heart movement of the patient is recorded.

3. The method as claimed in claim 1, wherein the overall recording area comprises an entire body of the patient.

4. The method as claimed in claim 1, wherein the movement status information is determined from navigator data of a pilot tone navigator.

5. The method as claimed in claim 1, wherein the slices that are recorded consecutively in time overlap one another.

6. The method as claimed in claim 5, wherein the slices that are recorded consecutively overlap by at least 80% or by at least 90%.

7. The method as claimed in claim 1, wherein the magnetic resonance data is recorded with a Dixon technique, wherein at least fat and water images for the movement status classes are determined to determine the attenuation maps from the magnetic resonance data.

8. The method as claimed in claim 1, wherein a Fast Low Angle Shot (FLASH) magnetic resonance sequence is used to record the magnetic resonance data.

9. The method as claimed in claim 1, wherein, based on the movement status information and/or the magnetic resonance data: individual partial image data sets of the PET image data set are assigned to the different movement status classes and combined to form a movement-corrected overall image data set as the PET image data set.

10. The method as claimed in claim 9, further comprising:
determining movement information describing a relative movement between movement status classes; and
performing movement correction, based on the movement information, for the movement status classes by registering the magnetic resonance data assigned to the different movement status classes.

11. A non-transitory computer-readable storage medium with an executable program stored thereon, that when executed, instructs a processor to perform a method for recording a positron emission tomography (PET) image data set of an overall recording area of a patient, the method comprising:
using a magnetic resonance PET device, simultaneously recording PET raw data, magnetic resonance data of corresponding slices of the patient currently located within a field of view of the magnetic resonance PET device, and movement status information relating to one of a plurality of cyclical movements of the patient, the overall recording area of the patient exceeding a size of the field of view of the magnetic resonance PET device, wherein the overall recording area for recording the PET raw data is moved continuously at a constant movement speed through the field of view;
assigning a movement status class, based on the movement status information, to the PET raw data and the magnetic resonance data associated with each of the plurality of cyclical movements;
based on the magnetic resonance data assigned to the different movement status classes:
determining attenuation maps of the patient for each of the different movement status classes, and
applying the attenuation maps to the PET raw data assigned to the corresponding one of the different movement status classes; and
reconstructing the PET image data set from the PET raw data based on at least one of the attenuation maps of the overall recording area.

12. A magnetic resonance positron emission tomography (PET) device for recording a PET image data set of an overall recording area of a patient, the device comprising:
a scanner; and
a controller in communication with the scanner, and configured to:
control the scanner to simultaneously record PET raw data, magnetic resonance data of corresponding slices of a patient currently located within a field of view of the magnetic resonance PET device, and movement status information relating to one of a plurality of cyclical movements of the patient, the overall recording area of the patient exceeding a size of the field of view of the magnetic resonance PET device, wherein the overall recording area for recording the PET raw data is moved continuously at a constant movement speed through the field of view;
assign a movement status class, based on the movement status information, to the PET raw data and the magnetic resonance data associated with each of the plurality of cyclical movements;
based on the magnetic resonance data assigned to the different movement status classes:
determine attenuation maps of the patient for each of the different movement status classes, and
apply the attenuation maps to the PET raw data assigned to the corresponding one of the different movement status classes; and
reconstruct the PET image data set from the PET raw data based on at least one of the attenuation maps of the overall recording area.

* * * * *